(12) United States Patent
Dutta Ray et al.

(10) Patent No.: US 11,766,519 B2
(45) Date of Patent: Sep. 26, 2023

(54) DRUG DELIVERY MECHANISM

(71) Applicant: AMGEN INC., Thousand Oaks, CA (US)

(72) Inventors: Sudeshna Dutta Ray, Thousand Oaks, CA (US); Scott R. Gibson, Granada Hills, CA (US); Daniel Eduardo Groszmann, Belmont, MA (US); Mehran Mojarrad, Thousand Oaks, CA (US); Robert Allen Dees, San Diego, CA (US); Jonathan Dean Johnson, San Marcos, CA (US); Antonio S. Murcia, Oceanside, CA (US)

(73) Assignee: AMGEN INC., Thousand Oaks, CA (US)

( * ) Notice: Subject to any disclaimer, the term of this patent is extended or adjusted under 35 U.S.C. 154(b) by 568 days.

(21) Appl. No.: 16/961,762

(22) PCT Filed: Jan. 17, 2019

(86) PCT No.: PCT/US2019/013905
§ 371 (c)(1),
(2) Date: Jul. 13, 2020

(87) PCT Pub. No.: WO2019/143753
PCT Pub. Date: Jul. 25, 2019

(65) Prior Publication Data
US 2021/0060259 A1    Mar. 4, 2021

Related U.S. Application Data

(60) Provisional application No. 62/618,288, filed on Jan. 17, 2018.

(51) Int. Cl.
*A61M 5/315* (2006.01)
*A61M 5/20* (2006.01)

(52) U.S. Cl.
CPC ...... *A61M 5/31511* (2013.01); *A61M 5/2033* (2013.01); *A61M 5/31583* (2013.01)

(58) Field of Classification Search
CPC ............ A61M 5/31511; A61M 5/2033; A61M 5/31583; A61M 5/14248;
(Continued)

(56) References Cited

U.S. PATENT DOCUMENTS 6,474,219 B2    11/2002  Klitmose et al.
6,482,186 B1    11/2002  Douglas et al.
(Continued)

FOREIGN PATENT DOCUMENTS

EP    1754498 A1    2/2007
EP    3260146 A1    12/2017

OTHER PUBLICATIONS

International Application No. PCT/US2019/013905, International Search Report and Written Opinion, dated Apr. 1, 2019.

*Primary Examiner* — Amber R Stiles
*Assistant Examiner* — Nelson Louis Alvarado, Jr.
(74) *Attorney, Agent, or Firm* — MARSHALL, GERSTEIN & BORUN LLP; Michael P. Furmanek

(57) ABSTRACT

A flexible plunger rod, drug delivery mechanism, drug delivery device, and methods are described that utilize the flexible plunger rod perform drug delivery operations. In embodiments, the flexible plunger rod can be stored in a curved configuration to thereby reduce a footprint of the drug delivery mechanism and device.

16 Claims, 6 Drawing Sheets

(58) Field of Classification Search
CPC ...... A61M 2005/31518; A61M 5/1452; A61M 5/31586
See application file for complete search history.

(56) References Cited

U.S. PATENT DOCUMENTS

| | | |
|---|---|---|
| 8,211,062 B2 | 7/2012 | Estes et al. |
| 2012/0218740 A1* | 8/2012 | Estes ........................ F04D 29/00 362/101 |
| 2017/0340827 A1 | 11/2017 | Nazzaro et al. |
| 2017/0340837 A1* | 11/2017 | Nazzaro ............ A61M 5/31593 |

* cited by examiner

DRUG DELIVERY MECHANISM

CROSS-REFERENCE TO RELATED APPLICATION

This is the United States National Phase of PCT/US19/13905, filed on Jan. 17, 2019, which claims the priority benefit of U.S. Provisional Application No. 62/618,288, filed on Jan. 17, 2018, the entire contents of each of which are hereby incorporated herein by reference.

FIELD OF THE DISCLOSURE

The present disclosure generally relates to drug delivery devices and, more particularly, to delivery mechanisms for drug delivery devices.

BACKGROUND

Some drug delivery devices include a reservoir for containing a drug and a delivery system that pushes the drug out of the reservoir using a plunger and a plunger rod. Conventional plunger rods can be rigid such that the rod projects rearwardly from the reservoir prior to an injection operation. This configuration can impact a size and footprint for the drug delivery device. Further, the drive mechanism for moving rigid plunger rods can be complicated and costly to manufacture.

SUMMARY

As set forth in more detail below, the present disclosure sets forth flexible plunger rods, as well as delivery mechanisms and drug delivery devices incorporating the flexible plunger rods, embodying advantageous improvements to lower manufacturing and material costs.

A delivery assembly for a drug delivery device is described herein that includes a reservoir having a tubular housing that extends along a longitudinal axis and has a delivery opening at a distal end. The delivery assembly further includes a plunger disposed within the reservoir in engagement with the housing and a flexible plunger rod operably coupled to the plunger. A feeding mechanism of the delivery assembly is coupled to the flexible plunger rod and configured to drive the flexible plunger rod along the longitudinal axis of the housing to drive the plunger towards the distal end.

In embodiments, the delivery assembly can include a plunger rod housing that has a curved interior extending therethrough to bend the flexible plunger rod in a storage configuration. The curved interior has a first opening disposed adjacent to the reservoir and a second, opposite opening disposed at an angle with respect to the first opening.

In embodiments, the flexible plunger rod can be a spring having a predetermined preload amount. In further embodiments, a coil member of the spring can have a circular cross section. In other embodiments, a coil member of the spring can have a rectangular cross-section.

In embodiments, the feeding mechanism can include a drive gear having a central opening for the spring to extend therethrough. The central opening has a thread that is configured to engage a spring of the flexible plunger rod such that rotation of the drive gear relative to the spring causes the spring to move longitudinally through the drive gear. In further embodiments, the feeding mechanism can further include a motor that has a driveshaft operably coupled to the drive gear and the delivery assembly can further include a controller that is configured to maintain a generally constant injection speed by controlling the operation of the motor. In further embodiments, the thread can include a shim that extends between adjacent coils of the spring or a threaded cavity that is configured to engage coils of the spring.

In embodiments, the delivery assembly can further include a stabilizer member extending within the flexible plunger rod and coupled thereto, the stabilizer member having an elongate body with a flat configuration to control flexing of the flexible plunger rod.

In embodiments, the delivery assembly can further include a coupling member that is mounted to an end of the flexible plunger rod. The coupling member and plunger have cooperating structures that are configured to engage one another and prevent rotation of the flexible plunger rod relative to the plunger.

A drug delivery device, such as an on-body drug delivery device or an autoinjector drug delivery device, is described herein that includes a delivery assembly of the above embodiments.

A method for dispensing a drug is described herein that includes driving a flexible plunger rod through an internal opening of a drive gear with a radially extending thread engaging the flexible plunger rod and driving a plunger longitudinally within a reservoir containing a drug with the flexible plunger rod.

In embodiments, driving the flexible plunger rod through the internal opening of the drive gear can include driving the flexible plunger rod through the internal opening of the drive gear with a shim extending through adjacent coils of the flexible plunger rod or with a thread cavity engaging coils of the flexible plunger rod.

In embodiments, the method can further include coupling the flexible plunger rod and the plunger with a coupling member, where the coupling member and plunger have cooperating structures such that, with the coupling member mounted to a distal end of the flexible plunger rod, the flexible plunger rod and plunger are restricted from rotating with respect to one another.

In embodiments, the method can further include storing the flexible plunger in a bent configuration.

In embodiments, the method can further include preloading the flexible plunger rod a predetermined amount.

In embodiments, the method can further include controlling operation of a motor having a driveshaft operably coupled to the drive gear to maintain generally constant rotation of the drive gear and thereby generally constant movement of the plunger and flexible plunger rod through the reservoir.

BRIEF DESCRIPTION OF THE DRAWINGS

The above needs are at least partially met through provision of the embodiments described in the following detailed description, particularly when studied in conjunction with the drawings, wherein.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

A flexible plunger rod, drug delivery mechanism, drug delivery device, and methods are described herein that utilize a flexible configuration to thereby lower manufacturing costs and decrease device size while providing exemplary drug delivery operations. More specifically, rather than a rigid plunger rod as utilized in conventional drug delivery devices, the embodiments described herein include a flexible plunger rod that can be stored in curved configuration to thereby reduce a footprint of the device. Additionally, a drive mechanism for such a flexible plunger rod can be simplified and less costly as compared to conventional mechanisms.

The present disclosure relates to drug delivery devices in general and provides two exemplary embodiments including an on-body injector and an autoinjector. The technology described herein, however, can also be incorporated into other suitable drug delivery devices.

Figure 1:
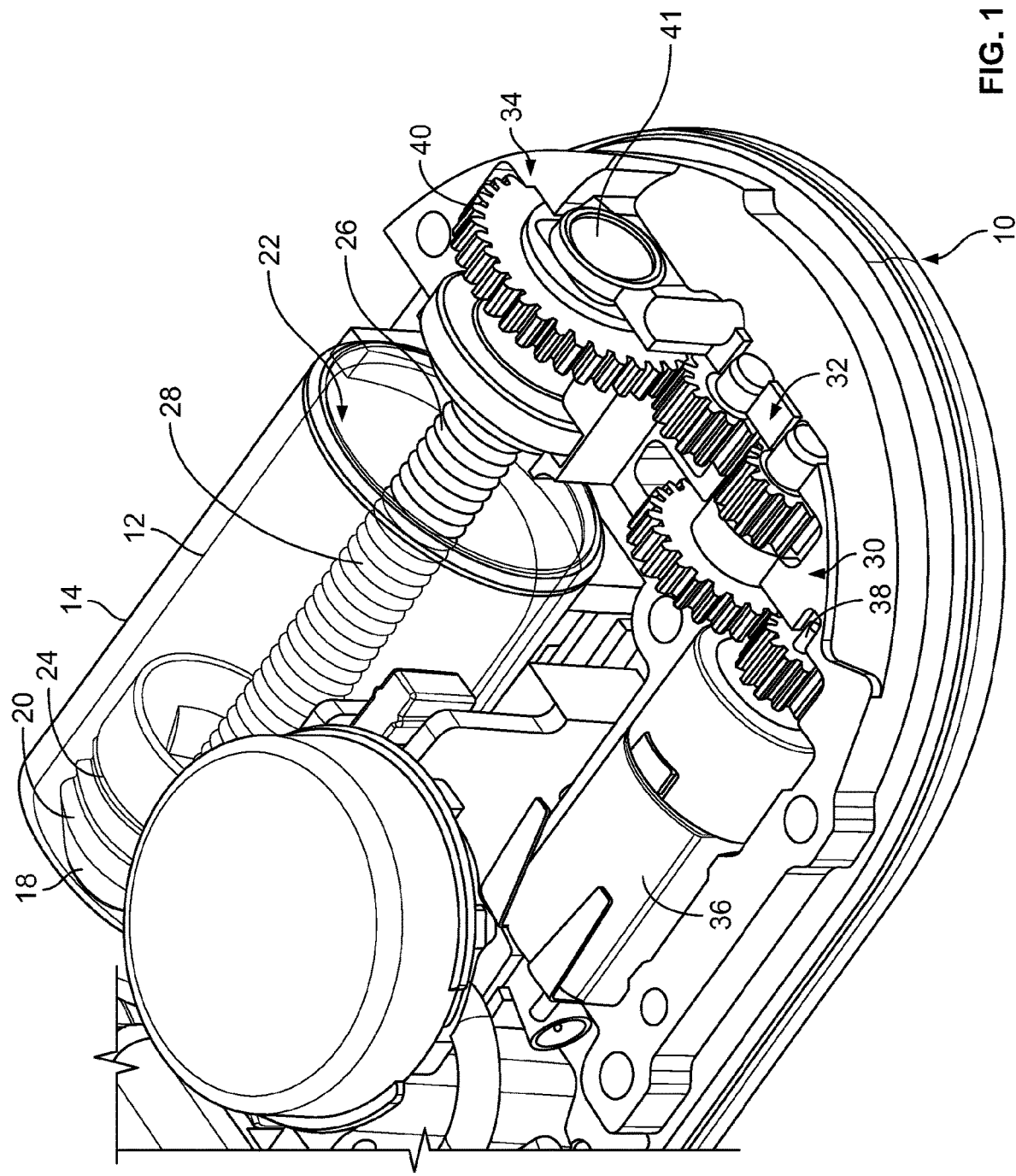
FIG. 1 is a perspective view of a delivery mechanism for a drug delivery device showing a first embodiment of a flexible plunger rod in accordance with various embodiments of the present disclosure.

A drug delivery assembly 10 is shown in FIG. 1 that includes a reservoir or cartridge 12 having a tubular housing 14 configured to store or contain a drug therein. The reservoir 12 includes a delivery opening 18 at a distal end 20 to deliver the drug to a cannula or other delivery structure (FIG. 10) and an open proximal end 22. A plunger 24 is disposed within the reservoir 12 adjacent to the proximal end 22 and engaged by a flexible plunger rod 26. As shown, the flexible plunger rod 26 is a spring that includes a coiled member 28. The coiled member 28 can have a generally circular cross-section as shown in FIG. 1, a rectangular cross-section as shown in FIG. 2, or other suitable shapes.

The spring of the plunger rod 26 can be an extension spring that is in a preloaded state such that the individual coils of the coiled member 28 are fully collapsed on one another without external forces acting on the spring and pulling the coils apart from one another requires a larger force than the preloaded amount. Advantageously, the preloaded amount can be adjusted to tailor the buckling characteristics of the spring so that the spring does not buckle during a drug delivery operation. For example, the preload amount can be in a range of about 0.5 pounds to about 3 pounds and, more preferably, in a range of about 0.75 pound to about 2 pounds, and more preferably, about 1 pound. Further, utilizing a coiled member 28 cross-sectional shape having flat sides, such as the rectangular configuration shown in FIG. 2, can aid in preventing undesirable buckling due to the adjacent surfaces abutting one another over a greater surface area than curved surfaces.

Figure 2:
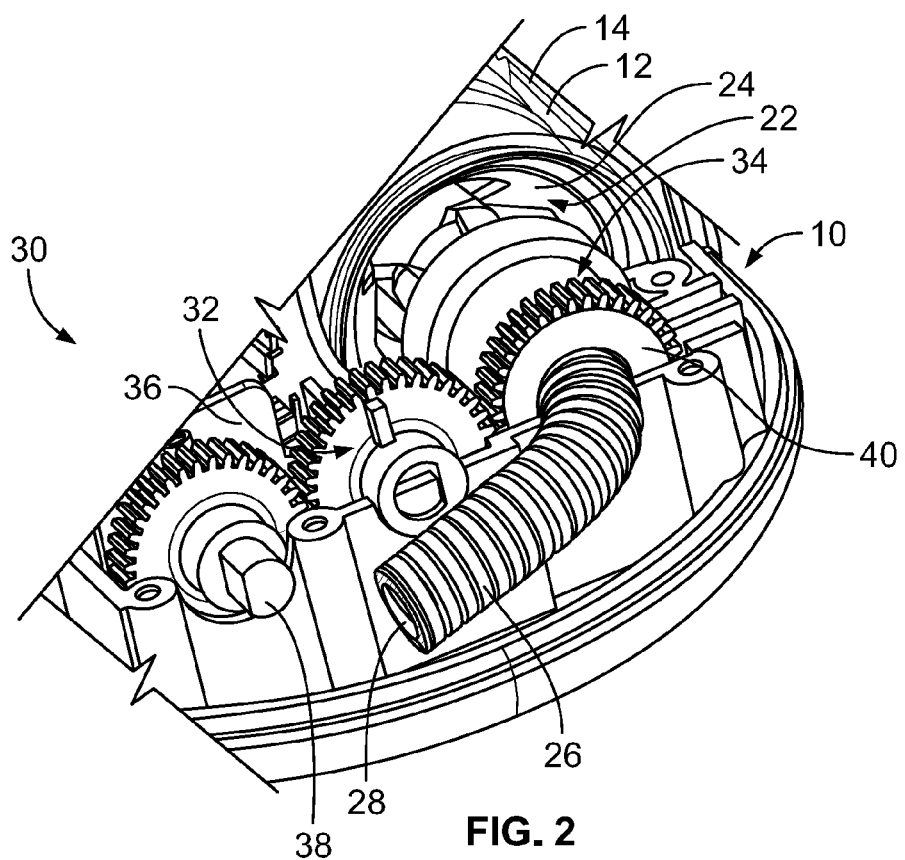
FIG. 2 is a perspective view of a delivery mechanism for a drug delivery device showing a second embodiment of a flexible plunger rod in accordance with various embodiments of the present disclosure.

As shown in FIGS. 1 and 2, movement of the plunger rod 26 is controlled by a drive mechanism 30 including a gear train 32 and a motor 36 having a drive shaft 38 coupled to the gear train 32 such that rotation of the drive shaft 38 causes rotation of the gears in the gear train 32. The gear train 32 can include gears of desired sizes to optimize gear ratios and the associated gear reduction for particular configurations. The gear train 32 includes a drive gear assembly 34 that engages the plunger rod 26 to drive the plunger rod 26 through the reservoir 12.

Figure 3:
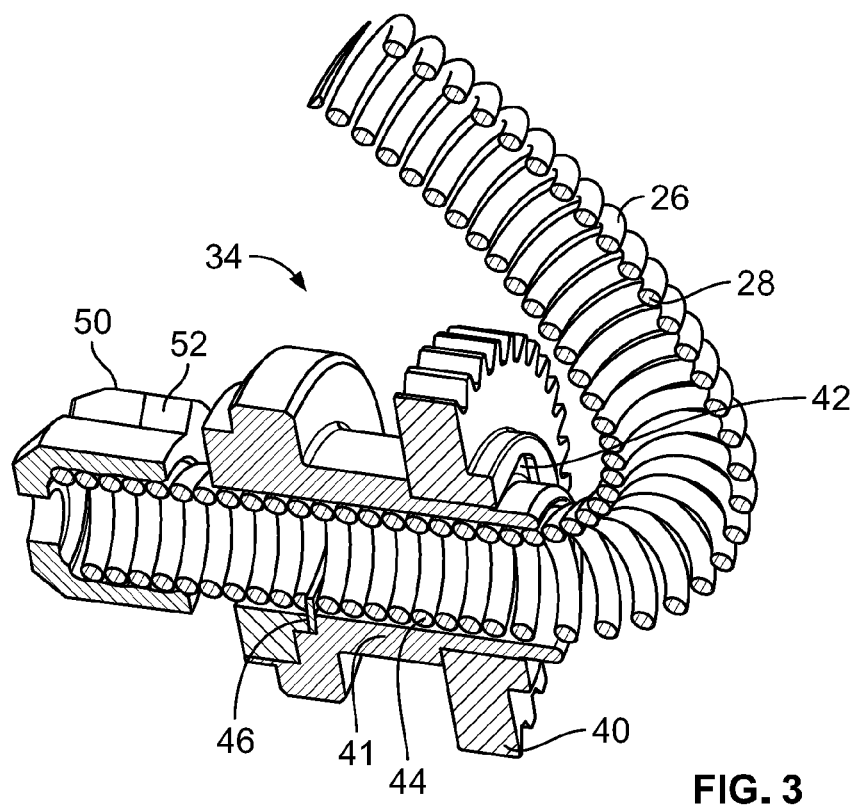
FIG. 3 is a cross-sectional view of a drive gear for the delivery mechanism of FIG. 1 or FIG. 2.

As shown in more detail in FIG. 3, the drive gear assembly 34 includes a drive gear 40 interconnected with the other gears of the gear train 32 and a plunger rod drive member 41 that is coupled to the drive gear 40 via interacting portions 42, such as a rectangular plug and corresponding opening as shown, to rotate along with the drive gear 40. The drive member 41 has a tubular configuration with an interior 44 that is sized so that the plunger rod 26 can extend through the drive member 41. A thread or shim 46 is integrated with or secured to the drive member 41, such that the shim 46 extends into the interior 44 of the drive member 41 and between adjacent coils in the spring of the plunger rod 26. So configured, when the drive gear 32 is rotated due to operation of the motor 36, the drive member 41 is also rotated and the shim 46 spins through the coils of the spring causing the plunger rod 26 to be driven longitudinally through the drive member 41 and through the reservoir 12.

Figure 4:
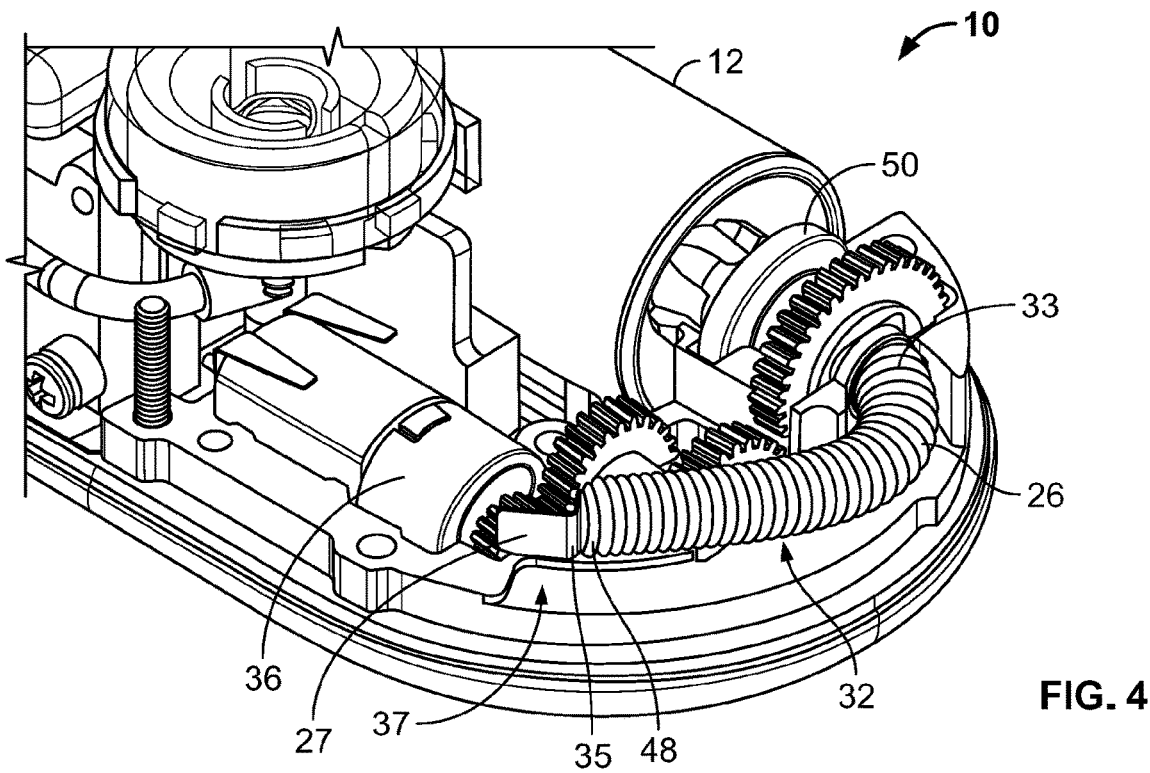
FIG. 4 is a perspective view of a delivery mechanism for a drug delivery device showing a stabilizer for a flexible plunger rod in accordance with various embodiments of the present disclosure.
Figure 5:
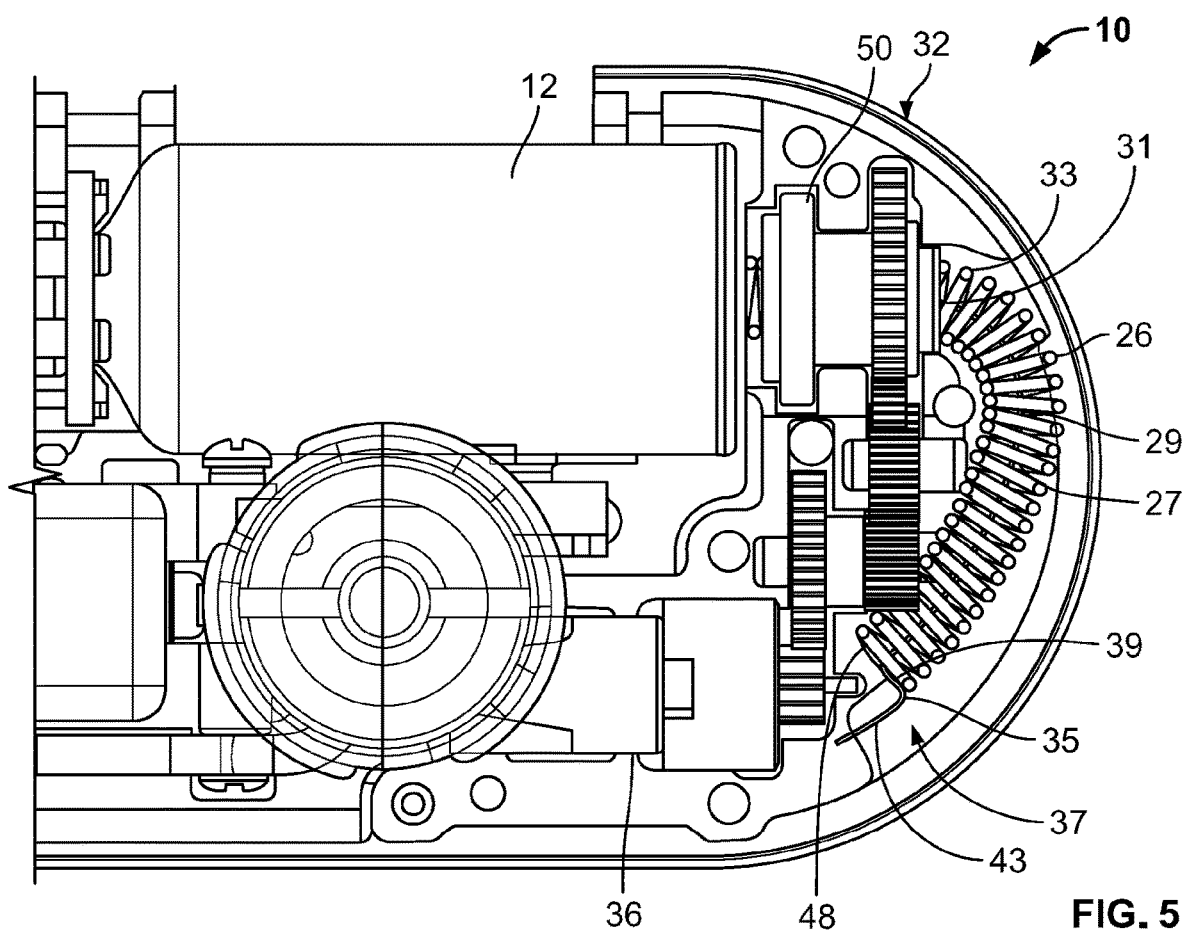
FIG. 5 is a top plan view of the delivery mechanism for a drug delivery device of FIG. 4.

If desired, as shown in FIGS. 4 and 5, the delivery assembly 10 can include a stabilizer 27 having an elongate body 29 with a flat configuration, such that the body 29 can be flexed along a plane perpendicular to the width of the body while also resisting being flexed along other planes. The stabilizer 27 is disposed within the flexible plunger rod 26 to control the flexure thereof. With this configuration, the stabilizer 27 allows the plunger rod 26 to have a curved storage position as shown in the figures and prevents the plunger rod 26 from rotating or buckling undesirably during storage and use. The body 29 extends between a proximal end 31 that is disposed adjacent to a proximal end 33 of the plunger rod 26 and a distal end 35 disposed adjacent to the distal end 48 of the plunger rod 26. By one approach, one or both of the ends 31, 35 of the stabilizer 27 can be secured, such as by welding, fasteners, adhesive, and the like, to a corresponding end 33, 48 of the plunger rod 26 to ensure that the stabilizer 27 travels with the plunger rod 26 as it is driven during operation. The distal end 35 of the stabilizer 27 can include a foot portion 37 with outwardly and rearwardly projecting portions 39, 43. The outwardly projecting portion 39 extends generally perpendicular to the body 29 to be disposed adjacent to the distal end 48 of the plunger rod 26 and secured thereto. The stabilizer 27 can be formed from any suitable material, such as sheet metal, a polymer, and so forth.

Figure 6:
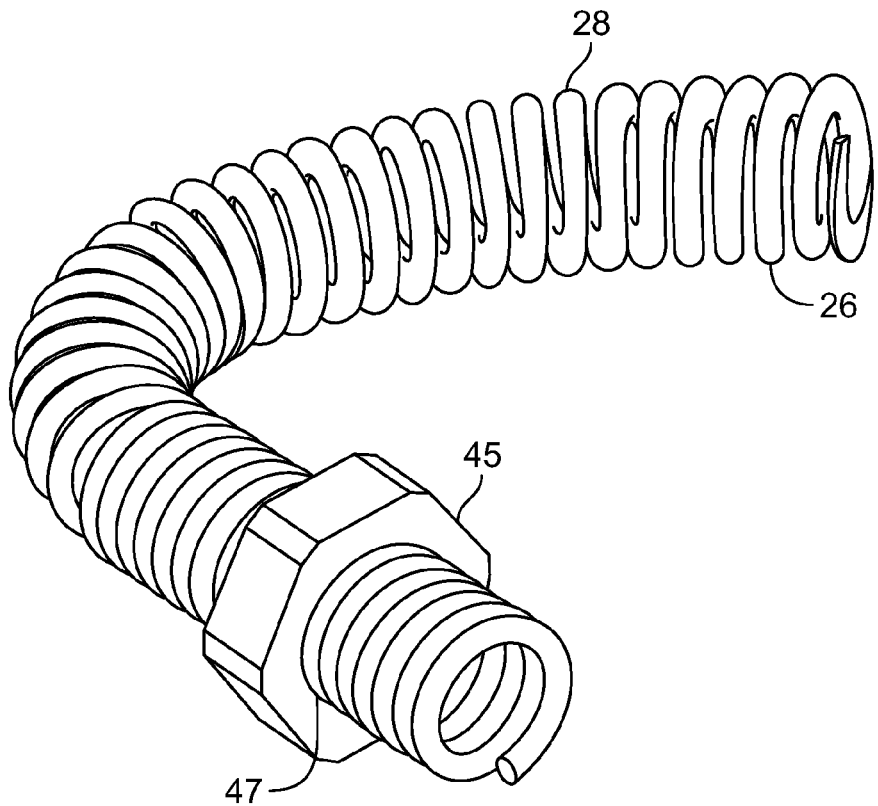
FIG. 6 is a perspective view of a flexible plunger rod and drive nut in accordance with various embodiments of the present disclosure.
Figure 7:
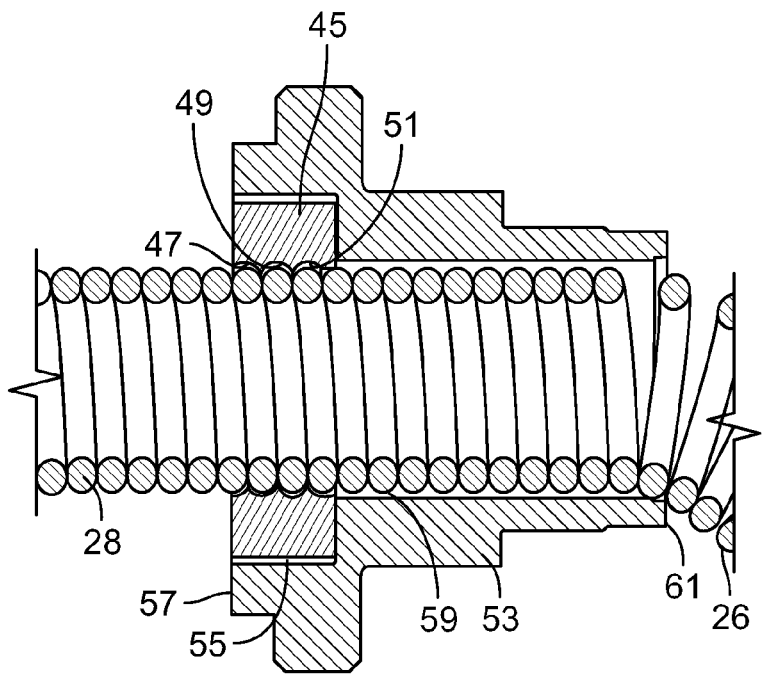
FIG. 7 is a cross-sectional view of the flexible plunger rod and drive nut of FIG. 6 mounted within a drive housing.

A drive member 45 providing an alternative to the drive member 41 and shim 46 described above is shown in FIGS. 6 and 7. In this form, the drive member 45 includes a central throughbore 47 sized to receive the plunger rod 26 therethrough. An interior surface 49 of the throughbore 47 includes a thread cavity 51 extending therearound configured to engage the coiled member 28 of the plunger rod 26, such that rotation of the drive member 45 causes the thread cavity 51 to drive the plunger rod 26 through the throughbore 47. To orient the plunger rod 26 within the drive member 45 during operation, the delivery assembly 10 can further include a housing 53 having a recess 55 in a distal end 57 thereof sized to receive drive member 45 and an elongate throughbore 59 extending from the recess 55 to a proximal end 61. The elongate throughbore 59 extends along an axis and is sized so that the portion of the plunger rod 26 engaging the thread cavity 51 is not flexed or curved. The drive member 45 can be secured within the recess 55 by any suitable mechanism, including welding, fasteners, friction, and so forth.

Figure 8:
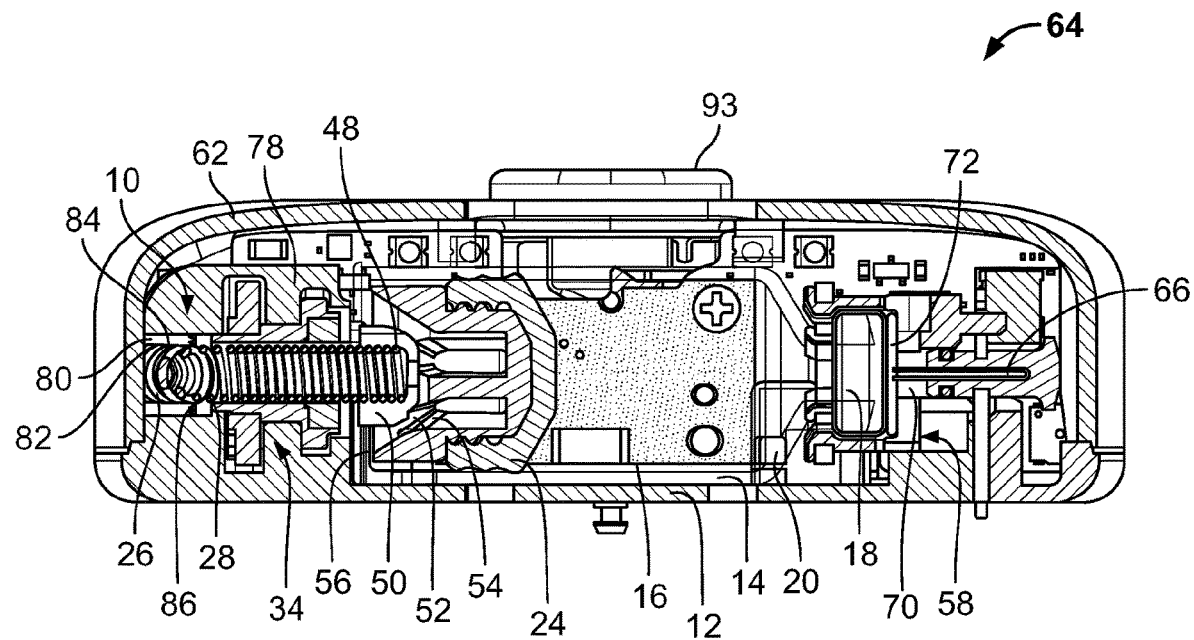
FIG. 8 is a side cross-sectional view of an on-body injector drug delivery device showing a delivery mechanism and a cartridge piercing assembly in accordance with various embodiments of the present disclosure.

Turning to FIG. 8, a distal end 48 of the plunger rod 26 fixedly couples to the plunger 24 so that the plunger rod 26 cannot rotate with respect to the plunger 24. This fixed coupling can have any suitable configuration. For example, the plunger rod distal end 48 can be secured to a coupling member 50 that includes structures 52 that interconnect with corresponding structures 54 on a rear end 56 of the plunger 24. By one approach, one of the structures 52, 54 can be splines and the other of the structures 52, 54 can be slots, such that, once the structures 52, 54 are interconnected, the disc 50 and plunger 24 cannot rotate with respect to one another. By another approach, the plunger rod distal end 48 can be embedded within or bonded to the plunger 24. With these configurations, the plunger rod 26 is prevented from rotating during a delivery operation by virtue of the friction between the plunger 24 and the reservoir 12. As such, all movement transferred to the plunger rod 26 by the drive gear assembly 34 is converted to longitudinal movement down the reservoir 12.

As illustrated in FIG. 8, the drug delivery assembly 10 and a cartridge piercing assembly 58 are disposed or mounted within a housing 62 for an on-body drug delivery device 64. The cartridge piercing assembly 58 includes a piercing needle 66 and a fluid flow path 70 coupled to the piercing needle 66. Further, as shown, the distal end 20 of the reservoir 12 tapers to the delivery opening 18 and a septum 72 extends over the delivery opening 18 to seal the reservoir 12 and maintain the sterility of a drug 16 therein.

With this configuration, when the device 64 is activated, a drive mechanism 68 shifts the reservoir 12 so that the piercing needle 66 is driven through the septum 72 to fluidly couple the flow path 70 with the reservoir 12. In an alternative approach, the piercing needle 66 can be shifted through the septum 72 to fluidly couple the flow path 70 with the reservoir 12. Thereafter, the drive mechanism 10 can operate to move the plunger 24 down the reservoir 12 to push the drug 16 through the piercing needle 66 and into the flow path 70.

The drug delivery device 64 can further include a gear box 78 enclosing or partially enclosing the gear train 32 and a spring housing or portion 80. Advantageously, due to the flexible plunger rod 26, the device housing 62 can have a smaller footprint than a housing having to enclose a rigid plunger rod that projects rearwardly from the reservoir 12. More particularly, the spring portion 80 can include a curved pathway or bore 82 that the plunger rod 26 extends along while in a storage state. The pathway 82 includes a curved sidewall 84 and a first end opening 86 adjacent to the reservoir 12. So configured, the spring portion 80 bends the flexible plunger rod 26 to a desired curved configuration within the housing 62 to thereby decrease a required longitudinal length. As should be understood, the pathway 82 can extend along any desired path to bend the plunger rod 26 in desired storage configurations, such as along a 45 degree angle, a 90 degree angle, a 135 degree angle, a 180 degree angle, and so forth.

Figure 9:
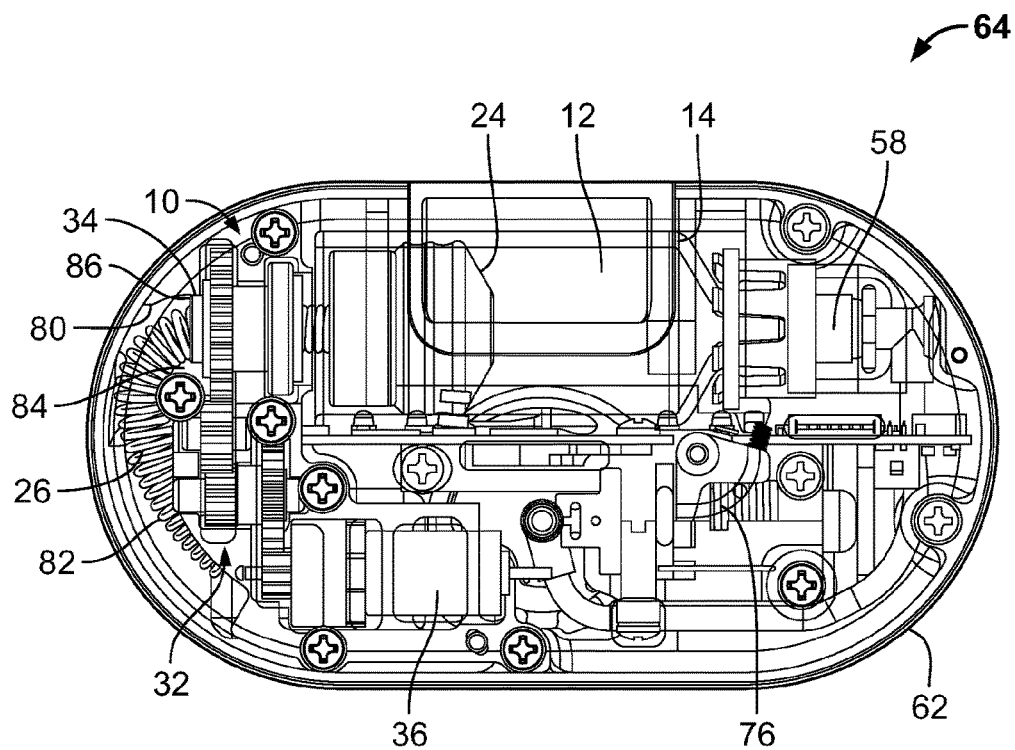
FIG. 9 is a top plan view of internal components of an on-body drug delivery device in accordance with various embodiments of the present disclosure.
Figure 10:
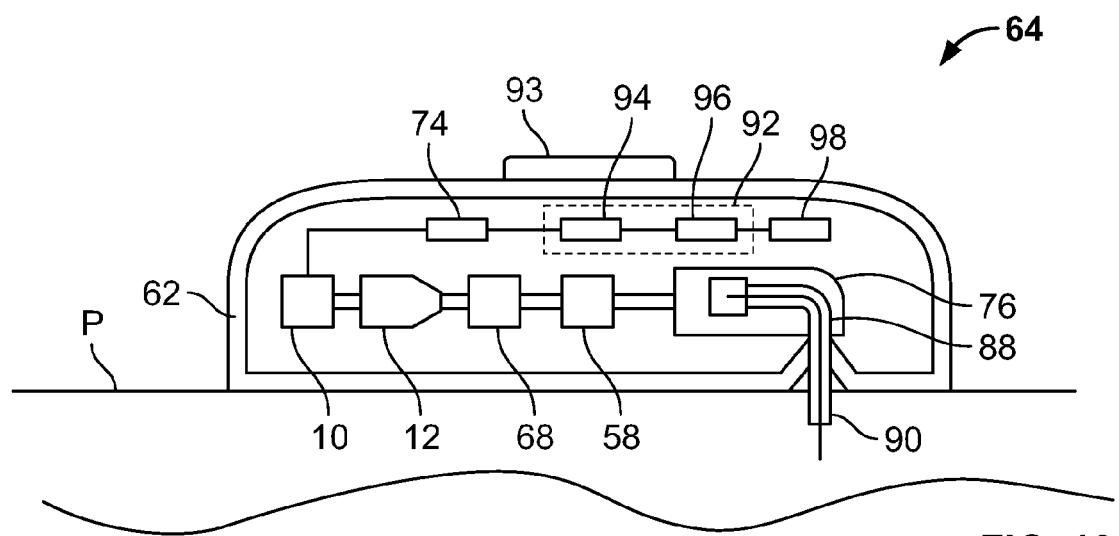
FIG. 10 is a side cross-sectional diagrammatic view of an on-body drug delivery device in accordance with various embodiments of the present disclosure.

As shown in FIG. 9, the housing 62 is sized to receive the delivery assembly 10, the cartridge piercing assembly 58, and a needle insertion assembly 76. A diagram of the needle insertion assembly 76 is shown in FIG. 10. Examples of needle insertion assemblies may be found in U.S. Pat. Nos. 7,144,384 and 7,128,727, which are incorporated by reference herein for all purposes. The needle insertion assembly 76 includes a cannula or needle 88 that is movable between a storage state (not shown) where the cannula 88 occupies a retracted position with a terminal end 90 concealed inside the housing 62 and a delivery state where the cannula 88 occupies an extended position where the terminal end 90 extends out of (e.g., projects from) the housing 62. Thus, when the drug delivery device 64 is placed onto a patient P, as in FIG. 10, and the occupies the delivery state, the terminal end 90 of the cannula 88 penetrates the skin of the patient P.

The device 64 also includes a controller 92 that is coupled to the delivery assembly 10, the cartridge piercing assembly 58, and the needle insertion assembly 76 to control operation of each of the assemblies. More specifically, the controller 92 operates the needle insertion assembly 76 to move the cannula 88 so that the terminal end 90 is injected to a desired subcutaneous position, operates the cartridge piercing assembly 58 to pierce the septum 72 to fluidly couple the flow path 70 to the reservoir 12, and operates the delivery assembly 10 to move the flexible plunger rod 26 to thereby drive the plunger 24 through the reservoir 12 and force the drug 16 into the flow path 70 and out of the cannula 88 into the patient P. If desired, the controller 92 can further be coupled to a user input or switch device 93, such as a pushbutton, touchscreen, and so forth, and be configured to operate the drug delivery device 64 in response to an actuation of the user input device 93.

The controller 92 may include a programmable processor 94 and a memory 96, and be coupled to a power supply 74. The memory 96 can store logic (e.g., programming) that is executable by the processor 94 for operating the drug delivery device 64. The controller 92 can be programmed prior to being disposed within the housing 62. In some embodiments, the controller 92 may not be reprogrammed after installation. In other embodiments, the controller 92 may be able to communicate with a remote device such as a controller, smart phone, etc., for reprogramming even after it is disposed and sealed within the housing 62.

By controlling operation of the delivery assembly 10, and the rotation of the gear train 32, the controller 92 can modulate the flow rate of the drug 16 into the patient. Accordingly, the controller 92 can be programmed for desired flow rates and/or be adjustable by a user to a desired flow rate. Additionally, the controller 92 can be programmed for a delayed delivery operation.

In some embodiments, the drug delivery device 64 can also include a communication module 98 disposed on-board the drug delivery device 64 and in communication with the controller 92. According to one embodiment, the communication module 98 may be a Bluetooth/Bluetooth Low Energy module. Alternatively, other protocols may be used by the communication module 98, such as RFID, Zigbee, Wi-Fi, NFC, and others. The controller 92 can be configured to cause the communication module 98 to transmit information to a remote computing device (e.g., a remote computer, tablet, smart phone, etc.), where that information regards the status of the device 64, such as reporting a delivery operation, performance characteristics of the motor 36, and so forth.

Figure 11:
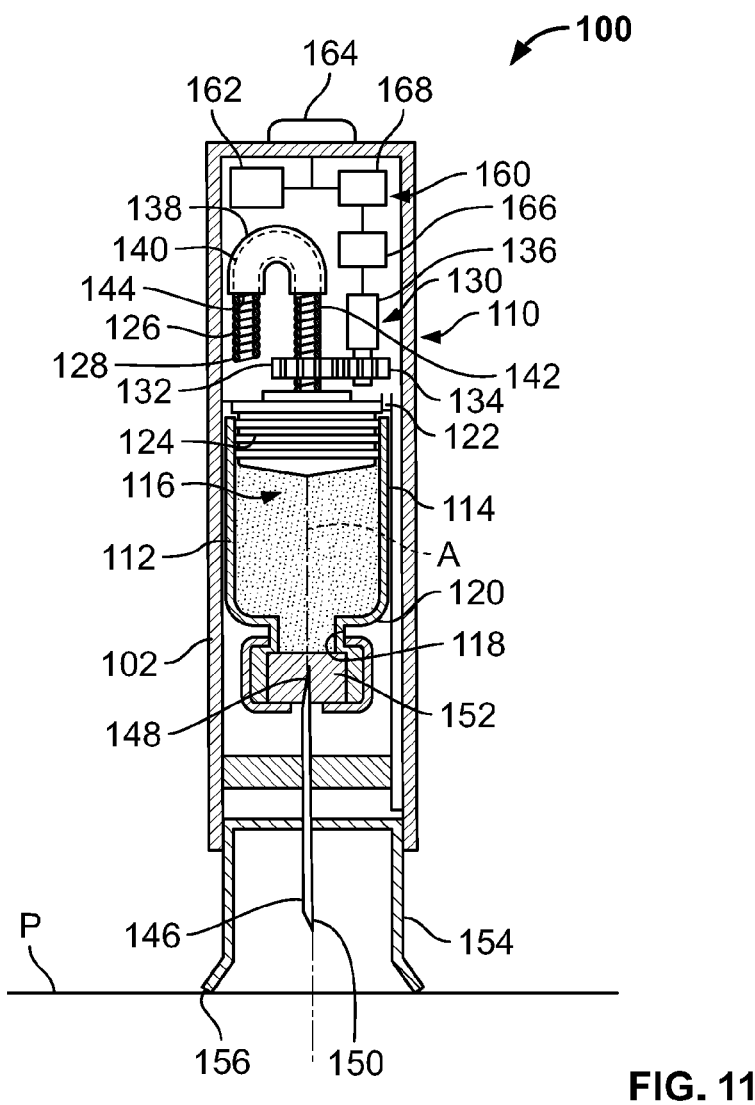
FIG. 11 is a side cross-sectional view of an autoinjector drug delivery device showing a flexible plunger rod in accordance with various embodiments of the present disclosure.

As shown in FIG. 11, a drug delivery assembly 110 configured similarly to the delivery assembly discussed above can be mounted or disposed within an autoinjector drug delivery device 100 having an elongate housing 102. The drug delivery assembly 110 includes a reservoir or cartridge 112 having a tubular housing 114 that is configured to store a drug 116 therein. The reservoir 112 includes a delivery opening 118 at a distal end 120 thereof and an open proximal end 122. A plunger 124 is disposed within the reservoir 112 adjacent to the proximal end 122 and engaged by a flexible plunger rod 126 having a coiled member 128. Similar to the above embodiment, movement of the plunger rod 126 is controlled by a drive mechanism 130 including a drive gear 132, a pinion gear 134, and a motor 136.

The autoinjector device 100 includes a spring housing 138 that, in this form, bends the flexible plunger rod 126 back upon itself to reduce a longitudinal length of the autoinjector device 100. As shown, the spring housing 138 includes a curved bore or interior 140 extending therethrough. The bore 140 includes a first end opening 142 adjacent to the reservoir 112 and a second, opposite end opening 144 oriented at an angle with respect to the first end opening 142. For example, the second end opening 144 can be oriented at about a 180 degree angle with respect to the first end opening 142 as shown in FIG. 11.

The autoinjector device 100 can include one or more assemblies or structures that insert or enable insertion of a cannula 146 into the patient P along an axis A along which the cannula 146 extends. A first end 148 of the cannula 146 may be connected or connectable in fluid communication to the reservoir 112 and a second end 150 that may be inserted into the patient P. The first end 148 of the cannula 146 may be disposed through a wall or septum 152 of the reservoir 112, and thus be connected in fluid communication with the reservoir 112. As illustrated, the first end 148 of the cannula 146 may be disposed only partially through the wall 152 such that the cannula first end 148 may not be connected in fluid communication with the reservoir 112 until the second end 150 is inserted into the patient. So configured, the wall 152 of this embodiment serves as a lock that maintains sterility of the reservoir 112. Moreover, in some embodiments, once removed from the patient, the cannula first end 148 may again become disconnected from fluid communication with the reservoir 112. In such a circumstance, the first end 148 may be described as connectable in fluid communication with the reservoir 112, although it will be recognized that there are other mechanisms by which the cannula first end 148 may be connectable, but not connected, in fluid communication with the reservoir 112.

If desired, the autoinjector device 100 can include a needle guard 154 to limit access to the cannula second end 150 when the autoinjector device 100 is not in use. According to certain embodiments, the needle guard 154 may have a biasing element (not shown) that urges the needle guard 154 away from the housing 102 and into a protracted position, as shown in FIG. 11, such that a distal end 156 of the needle guard 154 extends beyond the cannula second end 150 until if and when the cannula 146 is inserted into a patient. In fact, the injection of the cannula 146 may be actuated according to certain embodiments of the autoinjector device 100 by disposing the distal end 156 of the needle guard 154 on or against the skin of the patient P and applying a downward force.

The autoinjector device 100 may further include a controller 160 coupled to a communication module 162 for performing notification and communication actions similar to those described above with respect to the above embodiment and a user input device 164. The controller 160 can include a processor 166 and a memory 168 storing logic that is executable by the processor 166.

The processor 166 may be programmed to carry out certain actions that the controller 160 is adapted to perform and the memory 168 may include one or more tangible non-transitory readable memories having logic (e.g., executable instructions) stored thereon, which instructions when executed by the processor 166 may cause the processor 166 to carry out the actions that the controller 160 is adapted to perform. Additionally, the controller 160 may include other circuitry for carrying out certain actions in accordance with the principles of the present disclosure.

Based on the foregoing, the autoinjector device 100 in FIG. 11 has a storage state as shown and a delivery state (not shown) where the second end 150 of the cannula 146 extends beyond the distal end 156 of the needle guard 154. After the second end 150 of the cannula 146 is moved to a desired subcutaneous position within the patient P, the user can actuate the user input device 164 to cause the controller 160 to activate the motor 136 to rotate the pinion gear 134 and drive gear 132 to drive the flexible plunger rod 126 into the reservoir 112. The plunger rod 126, engaged with the plunger 124, such as with a disc 150 configured as discussed above, drives the plunger 124 through the reservoir 112 to thereby expel the drug 116 into the cannula 146 and, subsequently, the patient P.

Numerous alternatives and configurations for the above embodiments are within the scope of this disclosure. For example, although spring housings were described above to bend the flexible plunger rods 26, 126 while in a storage configuration, the devices 64, 100 can also utilize the flexible plunger rods 26, 126 in a straight configuration. Additionally, the spring of the plunger rod 26, 126 can have any desired diameter, such as ⅛ inch, ¼ inch, ⅜ inch, ½ inch, and so forth. Further, although preloading the spring is described above, the reservoir 112 can have a diameter sized to prevent buckling or can include an internal tubular portion having a diameter sized to prevent buckling. In other embodiments, instead of a motor, the drive mechanism can utilize one or more springs, a source of pressurized gas or a source of a material that undergoes a phase change, such that the escaping gas or phase changing material that provides a motive force, or any other electromechanical system. By another approach, rather than rotating the shim 46 to drive the plunger rod 26, 126, the motor 36, 136 can spin the plunger rod 26, 126. In this form, the connection between the plunger rod 26, 126 and the plunger 24, 124 can include a bearing member. Further, the motor 36, 136 can be movable to follow the longitudinal movement of the plunger rod 26, 126 can the connection therebetween can include an expanding or telescoping member.

The above description describes various devices, assemblies, components, subsystems and methods for use related to a drug delivery device. The devices, assemblies, components, subsystems, methods or drug delivery devices can further comprise or be used with a drug including but not limited to those drugs identified below as well as their generic and biosimilar counterparts. The term drug, as used herein, can be used interchangeably with other similar terms and can be used to refer to any type of medicament or therapeutic material including traditional and non-traditional pharmaceuticals, nutraceuticals, supplements, biologics, biologically active agents and compositions, large molecules, biosimilars, bioequivalents, therapeutic antibodies, polypeptides, proteins, small molecules and generics. Non-therapeutic injectable materials are also encompassed. The drug may be in liquid form, a lyophilized form, or in a reconstituted from lyophilized form. The following example list of drugs should not be considered as all-inclusive or limiting.

The drug will be contained in a reservoir. In some instances, the reservoir is a primary container that is either filled or pre-filled for treatment with the drug. The primary container can be a vial, a cartridge or a pre-filled syringe.

In some embodiments, the reservoir of the drug delivery device may be filled with or the device can be used with colony stimulating factors, such as granulocyte colony-stimulating factor (G-CSF). Such G-CSF agents include but are not limited to Neulasta® (pegfilgrastim, pegylated filgastrim, pegylated G-CSF, pegylated hu-Met-G-CSF) and Neupogen® (filgrastim, G-CSF, hu-MetG-CSF).

In other embodiments, the drug delivery device may contain or be used with an erythropoiesis stimulating agent (ESA), which may be in liquid or lyophilized form. An ESA is any molecule that stimulates erythropoiesis. In some embodiments, an ESA is an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin iota, epoetin omega, epoetin delta, epoetin zeta, epoetin theta, and epoetin delta, pegylated erythropoietin, carbamylated erythropoietin, as well as the molecules or variants or analogs thereof.

Among particular illustrative proteins are the specific proteins set forth below, including fusions, fragments, analogs, variants or derivatives thereof: OPGL specific antibodies, peptibodies, related proteins, and the like (also referred to as RANKL specific antibodies, peptibodies and the like), including fully humanized and human OPGL specific antibodies, particularly fully humanized monoclonal antibodies; Myostatin binding proteins, peptibodies, related proteins, and the like, including myostatin specific peptibodies; IL-4 receptor specific antibodies, peptibodies, related proteins, and the like, particularly those that inhibit activities mediated by binding of IL-4 and/or IL-13 to the receptor; Interleukin 1-receptor 1 ("IL-1-R1") specific antibodies, peptibodies, related proteins, and the like; Ang2 specific antibodies, peptibodies, related proteins, and the like; NGF specific antibodies, peptibodies, related proteins, and the like; CD22 specific antibodies, peptibodies, related proteins, and the like, particularly human CD22 specific antibodies, such as but not limited to humanized and fully human antibodies, including but not limited to humanized and fully human monoclonal antibodies, particularly including but not limited to human CD22 specific IgG antibodies, such as, a dimer of a human-mouse monoclonal hLL2 gamma-chain disulfide linked to a human-mouse monoclonal hLL2 kappa-chain, for example, the human CD22 specific fully humanized antibody in Epratuzumab, CAS registry number 501423-23-0; IGF-1 receptor specific antibodies, peptibodies, and related proteins, and the like including but not limited to anti-IGF-1R antibodies; B-7 related protein 1 specific antibodies, peptibodies, related proteins and the like ("B7RP-1" and also referring to B7H2, ICOSL, B7h, and CD275), including but not limited to B7RP-specific fully human monoclonal IgG2 antibodies, including but not limited to fully human IgG2 monoclonal antibody that binds an epitope in the first immunoglobulin-like domain of B7RP-1, including but not limited to those that inhibit the interaction of B7RP-1 with its natural receptor, ICOS, on activated T cells; IL-15 specific antibodies, peptibodies, related proteins, and the like, such as, in particular, humanized monoclonal antibodies, including but not limited to HuMax IL-15 antibodies and related proteins, such as, for instance, 146B7; IFN gamma specific antibodies, peptibodies, related proteins and the like, including but not limited to human IFN gamma specific antibodies, and including but not limited to fully human anti-IFN gamma antibodies; TALL-1 specific antibodies, peptibodies, related proteins, and the like, and other TALL specific binding proteins; Parathyroid hormone ("PTH") specific antibodies, peptibodies, related proteins, and the like; Thrombopoietin receptor ("TPO-R") specific antibodies, peptibodies, related proteins, and the like; Hepatocyte growth factor ("HGF") specific antibodies, peptibodies, related proteins, and the like, including those that target the HGF/SF:cMet axis (HGF/SF:c-Met), such as fully human monoclonal antibodies that neutralize hepatocyte growth factor/scatter (HGF/SF); TRAIL-R2 specific antibodies, peptibodies, related proteins and the like; Activin A specific antibodies, peptibodies, proteins, and the like; TGF-beta specific antibodies, peptibodies, related proteins, and the like; Amyloid-beta protein specific antibodies, peptibodies, related proteins, and the like; c-Kit specific antibodies, peptibodies, related proteins, and the like, including but not limited to proteins that bind c-Kit and/or other stem cell factor receptors; OX40L specific antibodies, peptibodies, related proteins, and the like, including but not limited to proteins that bind OX40L and/or other ligands of the OX40 receptor; Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-?4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); Vectibix® (panitumumab), Xgeva® (denosumab), Prolia® (denosumab), Enbrel® (etanercept, TNF-receptor/Fc fusion protein, TNF blocker), Nplate® (romiplostim), rilotumumab, ganitumab, conatumumab, brodalumab, insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta® (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris® (eculizumab); pexelizumab (anti-C5complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Orthoclone OKT3® (muromonab-CD3, anti-CD3 monoclonal antibody); Procrit® (epoetin alfa); Remicade® (infliximab, anti-TNF? monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-?4integrin mAb); Valortim® (MDX-1303, anti-*B. anthracis* protective antigen mAb); ABthrax™; Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2R? mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNF? mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-?5?1 integrin mAb); MDX-010 (ipilimumab, anti-CTLA-4 mAb and VEGFR-1 (IMC-18F1); anti-BR3 mAb; anti-C. difficile Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFN? mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); BMS-66513; anti-Mannose Receptor/hCG? mAb (MDX-1307); anti-mesothelin dsFv-PE38 conjugate (CAT-5001); anti-PD1mAb (MDX-1106 (ONO-4538)); anti-PDGFR? antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; and anti-ZP3 mAb (HuMax-ZP3).

In some embodiments, the drug delivery device may contain or be used with a sclerostin antibody, such as but not limited to romosozumab, blosozumab, or BPS 804 (Novartis) and in other embodiments, a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab). In other embodiments, the drug delivery device may contain or be used with rilotumumab, bixalomer, trebananib, ganitumab, conatumumab, motesanib diphosphate, brodalumab, vidupiprant or panitumumab. In some embodiments, the reservoir of the drug delivery device may be filled with or the device can be used with IMLYGIC® (talimogene laherparepvec) or another oncolytic HSV for the treatment of melanoma or other cancers including but are not limited to OncoVEXGALV/CD; OrienX010; G207, 1716; NV1020; NV12023; NV1034; and NV1042. In some embodiments, the drug delivery device may contain or be used with endogenous tissue inhibitors of metalloproteinases (TIMPs) such as but not limited to TIMP-3. Antagonistic antibodies for human calcitonin gene-related peptide (CGRP) receptor such as but not limited to erenumab and bispecific antibody molecules that target the CGRP receptor and other headache targets may also be delivered with a drug delivery device of the present disclosure. Additionally, bispecific T cell engager (BITE®) antibodies such as but not limited to BLINCYTO® (blinatumomab) can be used in or with the drug delivery device of the present disclosure. In some embodiments, the drug delivery device may contain or be used with an APJ large molecule agonist such as but not limited to apelin or analogues thereof. In some embodiments, a therapeutically effective amount of an anti-thymic stromal lymphopoietin (TSLP) or TSLP receptor antibody is used in or with the drug delivery device of the present disclosure.

Although the drug delivery devices, assemblies, components, subsystems and methods have been described in terms of exemplary embodiments, they are not limited thereto. The detailed description is to be construed as exemplary only and does not describe every possible embodiment of the present disclosure. Numerous alternative embodiments could be implemented, using either current technology or technology developed after the filing date of this patent that would still fall within the scope of the claims defining the invention(s) disclosed herein.

Those skilled in the art will recognize that a wide variety of modifications, alterations, and combinations can be made with respect to the above described embodiments without departing from the spirit and scope of the invention(s) disclosed herein, and that such modifications, alterations, and combinations are to be viewed as being within the ambit of the inventive concept(s).

What is claimed is:
1. A delivery assembly for a drug delivery device, the delivery assembly comprising:

a reservoir having a tubular housing extending along a longitudinal axis and having a delivery opening at a distal end;

a plunger disposed within the reservoir in engagement with the housing;

a flexible plunger rod comprising a spring having a predetermined preload amount and being operably coupled to the plunger; and a feeding mechanism coupled to the flexible plunger rod and configured to drive the flexible plunger rod along the longitudinal axis of the housing to drive the plunger towards the distal end, the feeding mechanism including a drive gear assembly having a central opening for the spring to extend therethrough, the central opening including a thread configured to engage the spring such that rotation of the drive gear assembly relative to the spring causes the spring to move longitudinally through the drive gear assembly, wherein the thread includes a shim that is configured to extend between adjacent coils of the spring.

2. The delivery assembly of claim 1, further comprising a plunger rod housing portion having a curved sidewall configured to bend the flexible plunger rod in a storage configuration.

3. The delivery assembly of claim 1, wherein a coil member of the spring has a circular or rectangular cross section.

4. The delivery assembly of claim 1, wherein the thread comprises a threaded cavity configured to engage coils of the spring.

5. The delivery assembly of claim 1, wherein the feeding mechanism further comprises a motor having a driveshaft operably coupled to the drive gear assembly, and further comprising a controller configured to maintain a generally constant injection speed by controlling the operation of the motor.

6. The delivery assembly of claim 1, further comprising a coupling member mounted to a distal end of the flexible plunger rod, the coupling member and plunger having cooperating structures configured to engage one another and prevent rotation of the flexible plunger rod relative to the plunger.

7. The delivery assembly of claim 1, wherein a distal end of the flexible plunger rod is fixed to the plunger.

8. The delivery assembly of claim 1, further comprising a stabilizer member extending within the flexible plunger rod and coupled thereto, the stabilizer member having an elongate body with a flat configuration to control flexing of the flexible plunger rod.

9. A drug delivery device including the delivery assembly of claim 1.

10. The drug delivery device of claim 9, further comprising an insertion assembly including a cannula selectively fluidly connected to the reservoir.

11. The drug delivery device of claim 9 comprising an on-body or an autoinjector drug delivery device.

12. A method for dispensing a drug, the method comprising:

driving a flexible plunger rod, comprising a spring having a predetermined preload amount, through a central opening of a drive gear assembly, the central opening including a thread configured to engage the spring such that driving the flexible plunger rod includes rotating the drive gear assembly relative to the spring to cause the spring to move longitudinally through the drive gear assembly, wherein the thread includes a shim that is configured to extend between adjacent coils of the spring; and driving a plunger longitudinally within a reservoir containing a drug with the flexible plunger rod.

13. The method of claim 12, further comprising coupling the flexible plunger rod and the plunger with a coupling member, the coupling member and plunger having cooperating structures such that, with the coupling member mounted to a distal end of the flexible plunger rod, the flexible plunger rod and plunger are restricted from rotating with respect to one another.

14. The method of claim 12, further comprising storing the flexible plunger rod in a curved configuration.

15. The method of claim 12, further comprising preloading the flexible plunger rod a predetermined amount.

16. The method of claim 12, further comprising controlling operation of a motor having a driveshaft operably coupled to the drive gear assembly to maintain generally constant rotation of the drive gear assembly and thereby maintain generally constant movement of the plunger and flexible plunger rod through the reservoir.

\* \* \* \* \*